Figure 1:
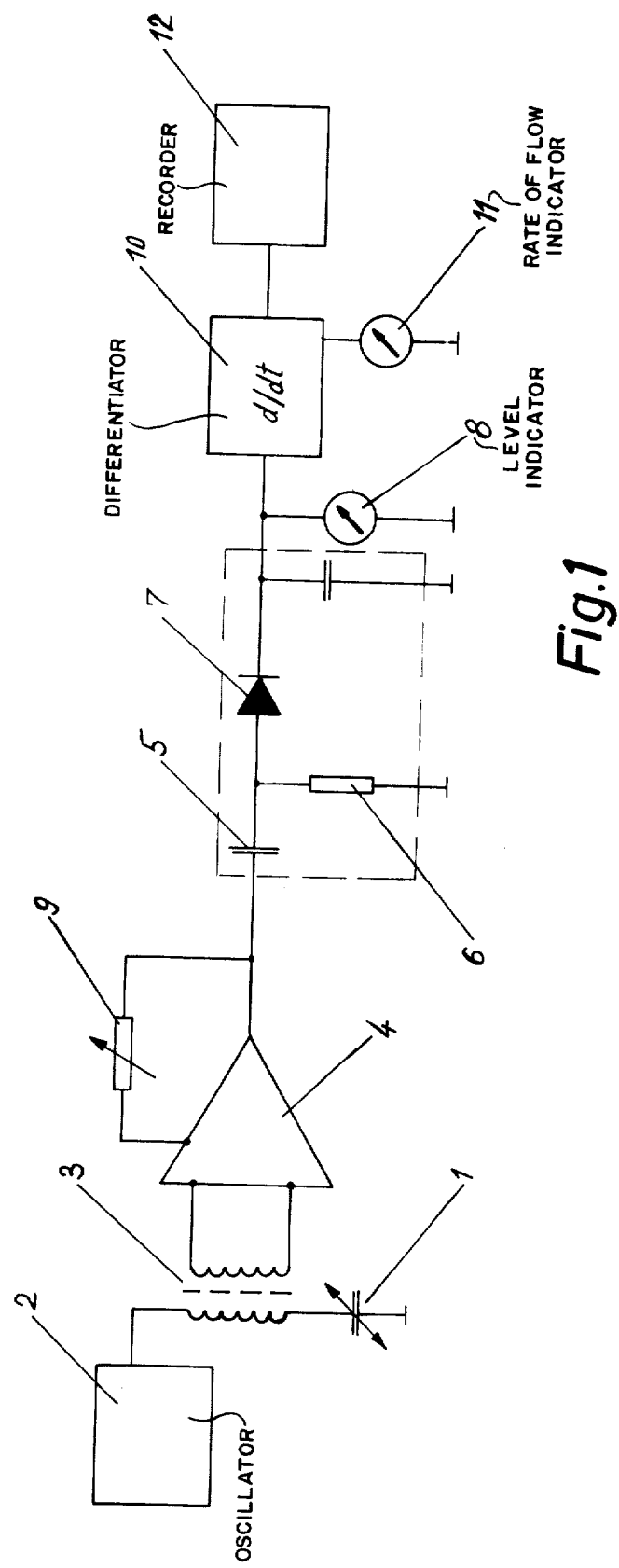

United States Patent [19]

Wurster

[11] 4,051,431

[45] Sept. 27, 1977

[54] APPARATUS FOR MEASURING RATES OF URINE FLOW ELECTRICALLY

[75] Inventor: Helmut Wurster, Oberderdingen, Germany

[73] Assignee: Richard Wolf GmbH, Knittlingen, Germany

[21] Appl. No.: 646,445

[22] Filed: Jan. 5, 1976

[30] Foreign Application Priority Data

Jan. 3, 1975 Germany .................. 2500094

[51] Int. Cl.² ............................................. G01R 27/26
[52] U.S. Cl. .............................. 324/61 R; 73/304 C; 73/194 E; 73/215
[58] Field of Search ................. 324/61 R; 73/304 C, 73/194 E, 215

[56] References Cited

U.S. PATENT DOCUMENTS

| 3,375,716 | 4/1968 | Hersch | 324/61 R X |
|---|---|---|---|
| 3,508,234 | 4/1970 | Snyder | 324/61 R X |
| 3,580,072 | 5/1971 | Cox et al. | 73/194 E X |
| 3,729,994 | 5/1973 | Klug | 73/215 X |
| 3,757,210 | 9/1973 | Hansen et al. | 324/61 R |
| 3,930,411 | 1/1976 | Beeker et al. | 73/304 C X |

FOREIGN PATENT DOCUMENTS

| 1,071,656 | 6/1967 | United Kingdom | 324/61 R |

Primary Examiner—Stanley T. Krawczewicz
Attorney, Agent, or Firm—Kinzer, Plyer, Dorn & McEachran

[57] ABSTRACT

This invention relates to apparatus for measuring the rate of flow F(t) of urine electrically using a measuring vessel whose filled volume V at any particular time is measured as a function V(t) of time t, so that the rate of flow $F(t) = dV/dt$ of the urine can be obtained by differentiating the time function.

In such apparatus, there is provided at least one electrical capacitor which is acted on by the amount of urine in the vessel and whose capacitance C(t) is influenced by the time-dependent amount of urine present, the urine acting both as an electrical conductor and as a di-electric, and the capacitance being used as an indication of the filled volume function which is to be differentiated electrically.

8 Claims, 4 Drawing Figures

APPARATUS FOR MEASURING RATES OF URINE FLOW ELECTRICALLY

The present invention relates to apparatus for measuring the rate of flow F(t) of urine electrically using a measuring vessel whose filled volume V at any particular time is measured as a function V(t) of time $t$, so that the rate of flow $F(t) = dV/dt$ of the urine can be obtained by differentiating the time function. Hereinafter such apparatus will be referred to as "of the kind described."

There are many kinds of measuring device for determining rates of urine flow. These may operate mechanically by making gravimetric measurements of urine volume using mechanical measuring sensors. Electrical methods of measurement on the other hand employ for this purpose, inter alia, electro-magnetic flow meters or a float which rests on the surface of the urine in the measuring vessel and carries a permanent magnet and which causes the magnet to induce in an external winding a current which is dependant on the change in the content of the vessel. This current is used as an indication of the flow rate.

It is also known to make use of the electrolytic conductivity of urine by allowing this conductivity to act on two resistors arranged in a measuring vessel. In this case the liquid being measured forms a partial bridge or short-circuit between an active, non-insulated resistor and an external electrode to produce, as a function of the height of the surface of the liquid, an effective, measured resistance which provides an indication of the filled volume at any given time. The other resistor is insulated and is used for temperature-compensating purposes.

Mechanical measuring devices are often highly complicated and troublesome both in construction and operation. The disadvantage of the majority of electrically operated devices is, inter alia, that they are difficult to clean. This necessarily creates source of error. Finally, errors may also result from the fact that it often happens, despite careful cleaning, that urine crystals short-circuit windings of the electrical resistors and thus give rise to incorrect measurements.

Accordingly, it is an object of the invention to provide apparatus of the kind described which is reliable in operation and gives accurate measurements and which is cheap and simple to construct and manufacture.

The invention consists in apparatus of the kind described wherein there is provided at least one electrical capacitor which is acted on by the amount of urine in the vessel and whose capacitance C(t) is influenced by the time-dependent amount of urine present, the urine acting both as an electrical conductor and as a di-electric and the capacitance being used as an indication of the filled volume function V(t) which is to be differentiated electrically. It is assumed that the apparatus is suitably calibrated to enable said capacitor to perform the stated function.

The capacitor is advantageously in the form of a co-axial tubular capacitor whose inner electrode is provided with an insulating coating, with the annular space formed between the two electrodes communicating with the space within the measuring vessel.

The liquid which rises in the said annular space in the course of the measuring process effects the capacitance of the measuring capacitor. This time-dependent change in capacitance is representative of the volume function V(t), and it thus function which is finally differentiated electrically to arrive at the desired value F(t).

Figure 2:
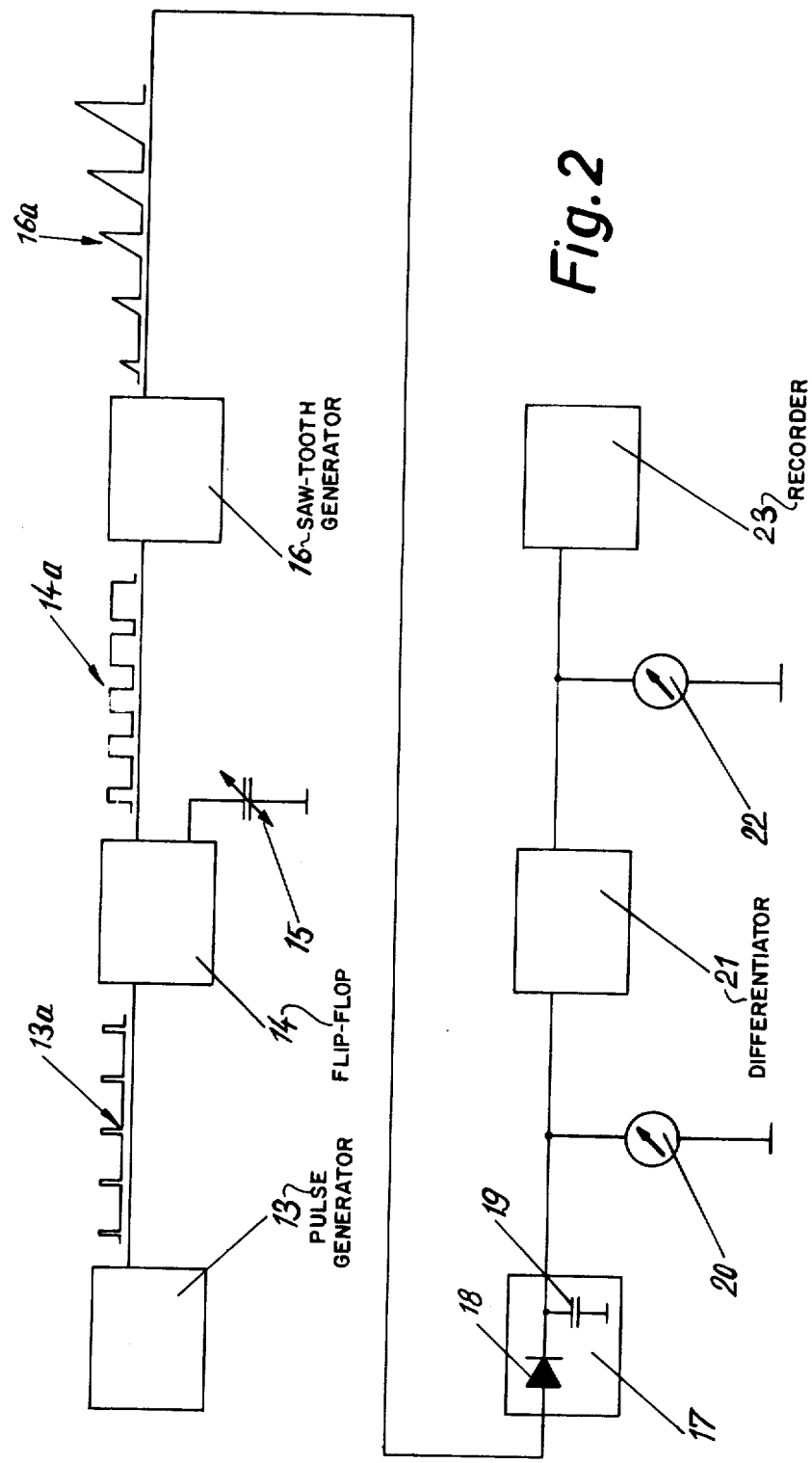
Figures 3, 4:
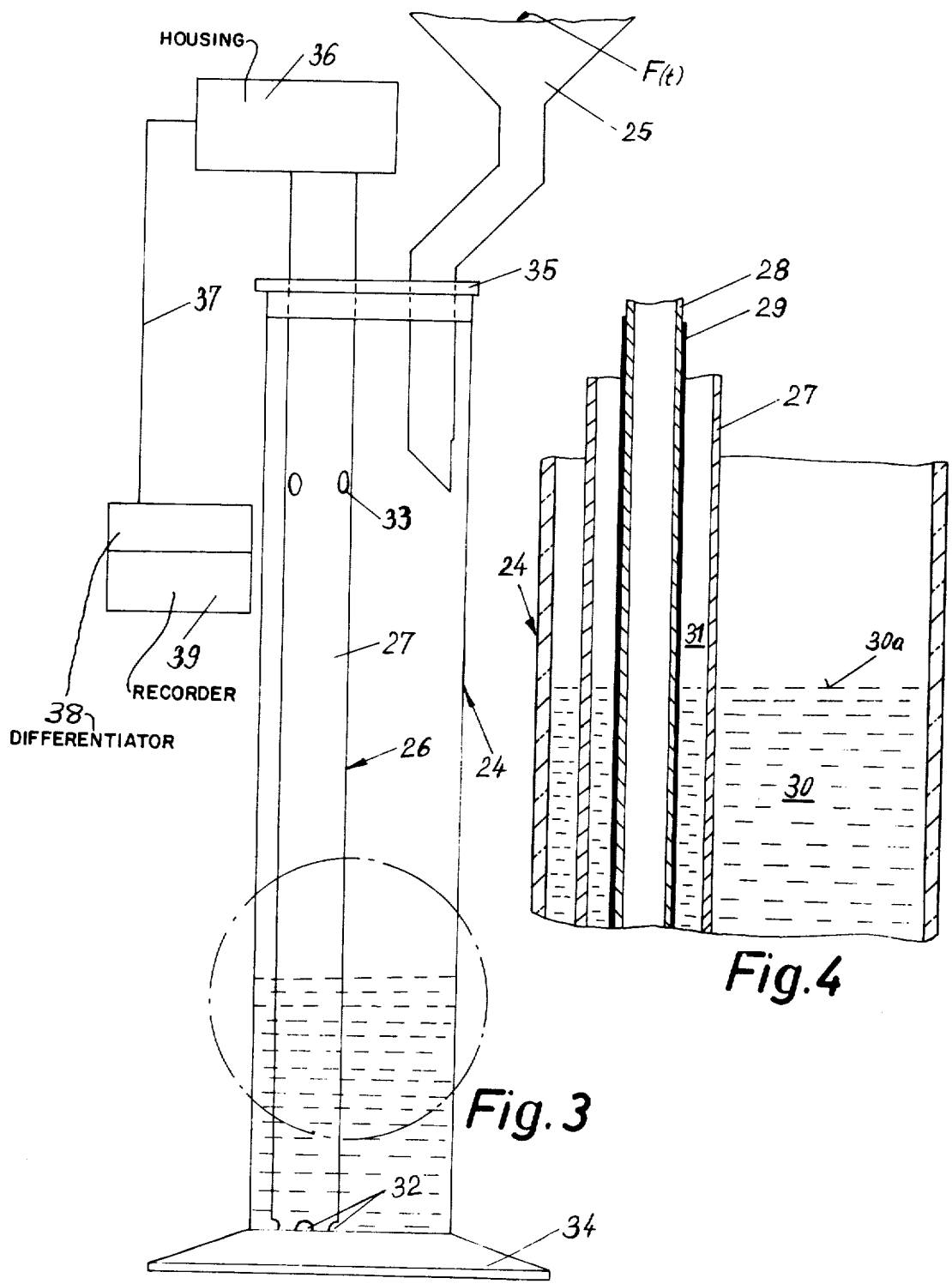

In order that the invention shall be more clearly understood, some embodiments thereof will now be described in conjunction with the accompanying drawings, in which:

FIG. 1 shows a first embodiment of electrical circuit for measuring and indicating rates of urine flow, FIG. 2 shows another embodiment of measuring circuit, FIG. 3 is a schematic side-view of a measuring apparatus and, FIG. 4 is a longitudinal section through part of the measuring vessel and the measuring capacitor, at the point where the circular area marked in chain lines in FIG. 3 is situated.

The rate of flow F(t) which is to be determined is obtained in the form $dV/dt$ by differentiating a value for filled volume V against time $t$. Since the capacitance C of the capacitor is proportional to the filled volume V in the case of the capacitive measurement according to the invention, C(t) is therefore indicative of F(t). The time-dependent and volume-dependent change in capacity C(t) may be determined by using it to influence an electrical value and making use of this electrical value. It is also possible to allow an electrical timing member to be acted on by the change in capacity, from whose output values for C(t) and thus values representative of F(t), may be extracted. Two practical embodiments illustrating these methods of measurement are shown in FIGS. 1 and 2.

Referring now to the drawings, in FIG. 1 a measuring capacitor 1 is fed with a constant AC voltage by an oscillator 2. The current flowing in the measuring capacitor thus represents a measurable electrical signal which is proportional to the volume function V(t). The larger the value of C, the smaller is the capacitive resistance and the greater is the current flow. By means of a transformer 3 the signal is transferred to the secondary side of the measuring circuit and passed on to an amplifier 4.

The AC voltage at a resistor 6, which arrives via a capacitor 5, is rectified by a rectifier 7 and measuring instrument 8 thus indicates an electrical magnitude which corresponds to the volume function V(t), provided of course that an adjustable calibrating resistor 9 has first been used to calibrate the measuring instrument, with the measuring circuit connected, in such a way that any particular filled volume in the measuring vessel is correlated with a specific electrical reading on instrument 8. The procedures required to do this are well known and therefore need not be explained in detail.

To arrive at F(t) from V (t), the V(t) signal is simply differentiated in a differentiating circuit 10, and the rate of urine flow F(t) which is to be determined can then be read off from measuring instrument 11. Connected to the differentiating circuit is a recorder 12 which allows a continuous written record of rates of flow over the measurement period to be obtained for the purpose of subsequent evaluation.

The measuring circuit shown in FIG. 2 employs a time-base in the form of a pulse generator 13 which, by means of pulses 13a of constant frequency operates a monostable flip-flop stage 14 which acts to time the length of pulses 14a. The measuring capacitor 15 is part of the timing circuit of the flip-flop stage, with the result that the length of the output pulses from the flip-flop changes as a function of the capacitance which exists at any particular time. In the present case the pulses 14a become longer for example as capacitance increases, although the frequency of the pulses remain constant and synchronised with the output signals from generator 13, of course.

The pulse-length modulated output signal represented by pulses 14a is fed to a saw-tooth generator 16 which converts it in a known way into a pulse-amplitude modulated signal 16a. This signal is rectified and smoothed in stage 17, by means of rectifier 18 and capacitor 19, with the result that in the present case also it is possible to read off a DC voltage proportional to volume function V(t) from a measuring device 20.

The function F(t) for rate of urine flow is obtained by electrical differentiation in a differentiating circuit 21, thus allowing F(t) to appear on a measuring instrument 22. Finally, the desired value F(t) is continuously recorded by means of recorder 23. In this case also it is necessary to perform an appropriate calibrating operation by assigning given indicated values to given filled volumes.

FIG. 3 shows the general lay-out of the apparatus as a whole. The apparatus consists of a measuring vessel 24 to which the urine is supplied via a funnel 25. The measuring capacitor is shown at 26 and is in the form of a co-axial tubular capacitor arranged in container 24 after the fashion of a measuring probe, being eccentrically or laterally located relative to the centre axis of the measuring vessel to save space.

The outer electrode of the measuring capacitor is formed by a metal cylinder 27 while the inner electrode is represented by a metal cylinder 28 which is fully insulated from the outer electrode 27 and from the urine 30 in measuring vessel 24 by a coating composed of an insulating material such as polytetrafluoroethylene. This prevents the liquid being measured from directly bridging the capacitor cylinders.

The annular space 31 between the two cylinders 27 and 28 communicates, via lower openings 32 in cylinder 27, with the remaining space in the measuring vessel, so that the level of the contents of the annular space will always be the same as that of the contents of the measuring vessel. Cylinder 27 also has, in the vicinity of its upper end, openings 33 through which the air in the annular space can escape as the liquid rises, thus enabling the liquid to flow without hindrance into the said annular space.

The tubular outer wall of measuring vessel 24, which is advantageously a laboratory-type measure, stands on a base 34 which may preferably be detached from it, while the opening at the top of the vessel is sealed by a plug or seal 35 through which the outlet tube at the bottom of the funnel and the cylindrical capacitor pass. At the top end of the cylindrical capacitor, part of the measuring circuitry shown in FIGS. 1 and 2 is mounted in a housing 36. This section of the circuitry is connected via a lead 37 to the external differentiating circuit 38 and the recorder 39, which latter components are likewise located in a common housing and may be set up at any suitable point.

When there is no urine to be measured in the measuring vessel, there are air and coating 29 between the cylindrical electrodes 27 and 28 to act as di-electrics. When the apparatus is calibrated, this condition is taken as the zero condition with V(t) = 0 and F(t) = 0. As soon as urine from the patient being examined reaches the measuring vessel 24 via funnel 25, the annular space 31 fills with urine in accordance with the volume function V(t), at which time the liquid level 30a rises. Because of this, the capacitance of measuring capacitor 26 becomes greater due to the fact that the liquid, as it rises between the electrodes of the capacitor, causes an increase in the di-electric constant.

This process is accompanied by a further capacity-raising effect which results from the fact that urine is an electrically conductive liquid. Thus, the active surfaces of the electrodes in the region beneath the surface 30a of the liquid can be looked upon as being, as it were, brought closer together by the liquid in annular space 31. The reason for this is that, effectively if not in fact, the inner face of the outer electrode 27 is transposed by means of the conductive liquid to rest against the outer periphery of coating 29 and the distance between the electrodes become smaller in the area mentioned, thus resulting in increased capacity. It is clear that basically, this supposition only applies directly and ideally in cases where the urine is of the same conductivity as the electrode 27. In all cases however the rising column of liquid between the electrodes of the capacitor gives rise to a change in capacitance both as a result of the marked alteration in the di-electric constant and also simply by its conductivity which, fundamentally, produces a change in the geometry of the capacitor.

The change in the capacitance of the measuring capacitor which is caused by the entry of urine into the measuring vessel is employed to determine F(t), using, for example, the circuits shown in FIGS. 1 and 2.

To clean the apparatus, the housing 36 may for example first be removed from the top end of the capacitor. In addition, the outlet tube from funnel 25 may be withdrawn from the seal 35 before the seal itself is removed. Capacitor 26 can then be withdrawn from seal 35 in its entirety. The inner electrode 28 can similarly be withdrawn from the outer electrode 27. Cleaning operations can then take place in the usual way using known means. The measuring cylinder is then emptied after the seal 35 has been taken off and is cleaned with similar ease. Since all these parts have smooth, even surfaces, they can be thoroughly, and above all easily, cleaned.

So that the capacitor can be accurately located in a given position in the measuring vessel when preparing for a fresh measuring operation, it is advantageous to provide in the base 34 a recess which is directed upwards and towards the interior of the measuring vessel and into which the lower ends of electrodes 27 and 28 are inserted and fixed.

Finally it should be mentioned that other methods of measurement may of course be considered besides the electrical ones described. In some cases these methods will be ones which detect changes in capacitance electrically in the form of magnitudes proportional to the volume function.

Also, the apparatus described is not restricted to a co-axial tubular configuration for the measuring capacitor. Although the embodiment of capacitor shown may be looked upon as the optimum for practical reasons, plate capacitors for example could also be used in which one of the electrode plates was provided with the insulating coating mentioned. This coating would then however have to be so arranged that it completely isolated the electrode concerned both from the liquid to be measured and from the other electrode.

I claim:

1. Apparatus of the kind described comprising a vessel for holding a changing volume (V) of urine having a flow rate (F(t)) to be measured in terms of $dV/dt$, an electrical capacitor submersible in the vessel and having a capacitance (C) which varies with the change of volume (V) in the vessel, means to charge the capacitor with an electrical current, an electrical circuit connected to the output of the capacitor to receive therefrom a signal which varies in accordance with the variation in capacitance C, and electrical differentiating means receiving said signal and deriving therefrom the urine flow rate equivalent.

2. Apparatus as claimed in claim 1, wherein the capacitor is supplied with substantially constant voltage via an oscillator and the current flowing through the capacitor, which represents the volume function V(t), is differentiated electrically.

3. Apparatus according to claim 2 having a transformer and an amplifier to which an electrical signal from the capacitor is delivered, a rectifier to which the amplified signal is fed, means feeding the rectified signal to the differentiating circuit, and means connected to the output of the differentiating circuit to record the flow rate of urine.

4. Apparatus as claimed in claim 1, wherein the changes in capacitance act on a timing member which is operated by control pulses and whose output pulses are used as an indication of the volume function V(t) which is to be electrically differentiated.

5. Apparatus according to claim 4 wherein the timing member is a monostable flip-flop stage, a constant frequency pulse generator operating said flip-flop, a sawtooth generator converting the output pulses from the timing member, a modulator modulating the output pulse in accordance with changes in capacitance into amplitude-modulated signals, and a rectifier changing said amplitude-modulated signals to DC voltage to be differentiated.

6. Apparatus according to claim 1 in which the capacitor includes two spaced electrodes one of which is coated with an insulator which isolates it from the other electrode and from the urine.

7. Apparatus as claimed in claim 6, wherein the capacitor is in the form of a co-axial tubular capacitor whose inner electrode is provided on the outside with said insulating coating, and the annular space formed between the two electrodes communicates with the interior of the measuring vessel.

8. A method of determining the flow rate (F(t)) of urine comprising, immersing an electrical capacitor in a vessel for receiving the urine, said capacitor having a capacitance which varies with the level of urine, interposing the capacitor in an electrical differentiating circuit which emits signals corresponding to the rate of change in capacitance, varied by the level of urine, and deriving from said signals the urine flow rate equivalent.

* * * * *